US008741957B2

(12) United States Patent
Salvati et al.

(10) Patent No.: US 8,741,957 B2
(45) Date of Patent: Jun. 3, 2014

(54) ALPHA-AMINOAMIDE DERIVATIVES USEFUL IN THE TREATMENT OF COGNITIVE DISORDERS

(75) Inventors: Patricia Salvati, Arese (IT); Stefano Rossetti, Varese (IT); Luca Benatti, Cologno Monzese (IT)

(73) Assignee: Newron Pharmaceuticals S.P.A., Bresso (MI) (IT)

( * ) Notice: Subject to any disclaimer, the term of this patent is extended or adjusted under 35 U.S.C. 154(b) by 1245 days.

(21) Appl. No.: 12/304,455

(22) PCT Filed: Jun. 13, 2007

(86) PCT No.: PCT/EP2007/005197
§ 371 (c)(1),
(2), (4) Date: Sep. 1, 2009

(87) PCT Pub. No.: WO2007/144153
PCT Pub. Date: Dec. 21, 2007

(65) Prior Publication Data
US 2010/0016437 A1    Jan. 21, 2010

(30) Foreign Application Priority Data

Jun. 15, 2006 (EP) ..................................... 06012352

(51) Int. Cl.
| A61K 31/165 | (2006.01) |
| A61K 31/404 | (2006.01) |
| A61K 31/085 | (2006.01) |
| A61K 31/135 | (2006.01) |
| A61K 31/341 | (2006.01) |
| A61K 31/402 | (2006.01) |

(52) U.S. Cl.
CPC ............. *A61K 31/404* (2013.01); *A61K 31/085* (2013.01); *A61K 31/135* (2013.01); *A61K 31/165* (2013.01); *A61K 31/341* (2013.01); *A61K 31/402* (2013.01)
USPC ........................................................ 514/620

(58) Field of Classification Search
CPC . A61K 31/085; A61K 31/135; A61K 31/165; A61K 31/341; A61K 31/402; A61K 31/404
USPC ........................................................ 514/640
See application file for complete search history.

(56) References Cited

U.S. PATENT DOCUMENTS

| 3,795,739 A | 3/1974 | Birkmayer et al. |
| 4,049,663 A | 9/1977 | Harper et al. |
| 4,513,009 A | 4/1985 | Roques et al. |
| 4,970,200 A | 11/1990 | Birkmayer et al. |
| 5,236,957 A | 8/1993 | Dostert et al. |
| 5,391,577 A | 2/1995 | Dostert et al. |
| 5,502,079 A | 3/1996 | Dostert et al. |
| 5,945,454 A * | 8/1999 | Pevarello et al. ............. 514/620 |
| 6,217,905 B1 | 4/2001 | Edgren et al. |
| 6,258,827 B1 | 7/2001 | Chenard et al. |
| 6,306,903 B1 | 10/2001 | Pevarello et al. |
| 6,479,484 B1 | 11/2002 | Lan et al. |
| 6,500,867 B1 | 12/2002 | Virkki et al. |
| 2002/0019421 A1 | 2/2002 | Biberman |
| 2005/0203130 A1* | 9/2005 | Buntinx ...................... 514/316 |
| 2007/0093495 A1 | 4/2007 | Ruggero et al. |

FOREIGN PATENT DOCUMENTS

| EP | 0400495 A1 | 12/1990 |
| GB | 1140748 | 1/1969 |
| WO | WO 90/14334 A | 11/1990 |
| WO | WO 90/14334 A1 | 11/1990 |
| WO | WO 94/22808 A | 10/1994 |
| WO | WO 97/05102 A | 2/1997 |
| WO | WO 97/05102 A1 | 2/1997 |
| WO | WO 2004/089353 A2 | 10/2004 |
| WO | WO 2005/102300 A1 | 11/2005 |

OTHER PUBLICATIONS

Kordower et al., Ann Neurol, 2001;49:202-213.*
Lanctot et al. CMAJ, 2003;169(6):557-564.*
Blanduni, F. et al., 1996, "Glutamate and Parkinson's disease," *Mol Neurobiol.* 12, 73-94.
Cattaneo et al., 2003, "Pressor Response to Intravenous Tyramine in Healthy Subjects After Safinamide, a Novel Neuroprotectant With Selective, Reversible Monoamine Oxidase B Inhibition," Clinical Neuropharmacology, 26(4), 213-217.
Jellinger, K. A., 1999, "Post mortem studies in Parkinson's disease-is it possible to detect brain areas for specific symptoms?", *J. Neural Transm.*, Suppl. 56,1-29.
Kishore et al., 1996, "Drug management of Parkinson's disease," *Canadian Family Physician* 42;946-952.
Krishnan, P. R. et al., 2003, "Restless legs syndrome in Parkinson's Disease: a case-controlled study," *Mov. Disord.*, 18, 181-185.
Office Action for U.S. Appl. No. 11/578,988 mailed Mar. 10, 2008.
Office Action for U.S. Appl. No. 11/578,988 mailed Dec. 11, 2008.
Office Action for U.S. Appl. No. 11/578,988 dated Aug. 17, 2009.
Pevarello, P. et al., 1998, Synthesis and Anticonvulsant Activity of a New Class of 2-[(Arylalkyl)amino]alkanamide Derivatives, *J. Med. Chemistry*, 41: 579-590.

(Continued)

Primary Examiner — San-Ming Hui
(74) Attorney, Agent, or Firm — Lucas & Mercanti, LLP

(57) ABSTRACT

The present invention is in the field of pharmacotherapy of cognitive deficits in learning and memory by administering an α-aminoamide, particularly safinamide. Examples of disturbances in cognition that can be treated with compounds of the invention are the ones associated with disorders such as autism, dyslexia, attention deficit hyperactivity disorder, schizophrenia, obsessive compulsive disorders, psychosis, bipolar disorders, depression, Tourette's syndrome, Mild Cognitive Impairment (MCI) and disorders of learning in children, adolescents and adults, Age Associated Memory Impairment, Age Associated Cognitive Decline, Alzheimer's Disease, Parkinson's Disease, Down's Syndrome, traumatic brain injury Huntington's Disease, Progressive Supranuclear Palsy (PSP), HIV, stroke, vascular diseases, Pick's or Creutzfeldt-Jacob diseases, multiple sclerosis (MS), other white matter disorders and drug-induced cognitive worsening.

11 Claims, No Drawings

(56) References Cited

OTHER PUBLICATIONS

Povedano et al. 2007, "Cognitive Function Impairment in Patients with Neuropathic Pain Under Standard Conditions of Care," *J. Pain Symptom Management*, 33(1), 78-89.
Response to Office Action for U.S. Appl. No. 11/578,988 mailed Mar. 10, 2008, filed on Aug. 11, 2008.
Office Action for U.S. Appl. No. 11/578,988 mailed Dec. 11, 2008, filed on Jun. 5, 2009.
Office Action for U.S. Appl. No. 11/578,988 dated Aug. 17, 2009, filed on Oct. 13, 2009.
Anonymous, "Newron Pharmaceuticals S.p.A. Announces Data of Phase I Clinical Trials of Its Anti-epileptic and Anti-Parkinson Compound NW-1015," Press Release of Mar. 14, 2000, Retrieved from the Internet: <URL: http://www.newron.com/uploads/Announcesdataofphase1clinicaltrials.pdf; retrieved on Feb. 18, 2009.
Anonymous: "Newron Releases Positive Preliminary Phase II Data for Salfinamide in Parkinson's Disease" Press Release of Jan. 9, 2003, Retrieved from the Internet: <URL: http://www.newron.com/uploads/SafinamidePhaseIIdataFinal090103.pdf retrieved on Feb. 18, 2009.
Archer, T. et al., 2002, "Restorative Effects of Glumate Antagonists in Experimental Parkinsonism," *Amino Acids*, 23:71-85.
Bailey et al., 1975, "The Mechanism of Action of Amantadine in Parkinsonism: A Review," *Arch. Int. Pharmacodyn. Ther.*, 216: 246-262.
Benedetti, S. et al., 1994, "The Anticonvulsant FCE 26743 is a Delective and Short-Acting MAO-B Inhibitor Devoid of Inducing Properties Towards Cytochrone P450-dependent Testosterone Hydroxylation in Mice and Rats," *J. Pharm. Pharmacol.* 46:814-819.
Chase, Thomas, 1998, "The Significance of Continuous Dopaminergic Stimulation in the Treatment of Parkinson's Disease, "*Drugs*, 55 (Suppl. 1): 1-9.
Chazot, P., 2001, "Salfinamide, Newron Pharmaceuticals," *Current Opinion in Invest. Drugs*, 2(6): 809-813.
Clarke, C. E., 2002, "Medical Management of Parkinson's Disease," J Neurol Neurosurg Psychiatry 72 (Suppl. 1) i22-i27.
Communication for European Patent Application 04 726 590.5-2123 mailed Dec. 5, 2006.
Facca, A, et al., 2003, "Differential Diagnosis of Parkinsonism," *Adv. Neurol*, 91:383-396.
Fariello et al., 1998, "Preclinical Evaluation of PNU-151774E as a Novel Anticonvulsant," *J. Pharmacol. Exp. Ther.* 285: 397-403.
Fredriksson et al, "Effects of co-administration of anticonvulsant and putative anticonvulsive agents and sub-suprathreshold doses of L-Dopa upon motor behaviour of MPTP-treated mice," Journal of Neural Transmission, vol. 106, Nos. 9-10, Oct. 1999, pp. 889-909.
Heikkila, R. et al., 1984, "Protection Against the Dopaminergic Neurotoxicity of 1-Methyl-4-Phenyl-1,2,5,6-Tetrahydropyridine by Monoamine Oxidase Inhibitors," *Nature* 311: 467-469.
International Preliminary Examination Report and Written Opinion of PCT/IB2004/001408.
International Search Report of PCT/IB2004/001408.
Lees, A. J., 2002, "Drugs for Parkinson's Disease," *J Neurol Neurosurg Psychiatry* 73:607-610.
Letter regarding Oral Proceedings for European Patent Application 04 726 590.5-2123 dated Oct. 19, 2007.
Maj, R. et al., 1999, "PNU-141774E, A Combined MAO-B and Glutamate Release Inhibitor, is Effective in Animal Models of Parkinson's Disease," Society for Neuroscience, vol. 25, p. 1599.
Mann et al., 1971, "Amantadine for Parkinson's Disease, "*Neurology*, 21: 958-962.
Marjama-Lyons, J. et al., 2001, "Parkinson's Disease: Update in Daignosis and Symptom Management," *Geriatrics* Aug; 56(8):24-25, 29-30, and 33-35.
Marsden et al; 1997, "Success and Problems of Long-Term Levodopa Therapy in Parkinson's Disease," *Lancet* Feb. 12, 1997: 345-349.
Meldrum, B., 1994, "The Role of Glutamate in Epilepsy and Other CNS Disorders," *Neurology*, 44 (Supp. 8) 814-823.
Minutes of Oral Hearing (Jan. 25, 2008) for EP 04 726 590.5-2123.

Mytilineou, C. et al., 1997, "L-Deprenyl Protects Mesencephalic Dopamine Neurons from Glutamate Receptor-Mediated Toxicity in Vitro," *J. Neurochem*. 68: 33-39.
Office Action for U.S. Appl. No. 10/559,982 mailed Oct. 15, 2008.
Office Action for U.S. Appl. No. 10/559,982 mailed Dec. 24, 2008.
Office Action for U.S. Appl. No. 10/559,982 dated Sep. 17, 2009.
Parkes, J. D, et al., 1971, Treatment of Parkinson's Disease with Amantadine and Levodopa,: *Lancet*, 21: 1083-1086.
Poewe, W., 1993, "Clinical Features, Diagnosis, and Imaging of Parkinsonian Syndromes," *Curr Opin Neurol Neurosurg*, Jun, 6(3):333-338.
Remington's Pharmaceutical Sciences 15th Edition, pp. 1035-1038 and 1570-1580.
Reply to Examination Report for European Patent Application 04 726 590.5-2123 dated Aug. 9, 2006.
Reply to Examination Report for European Patent Application 04 726 590.5-2123 dated Apr. 6, 2007.
Salvati, P. et al., 1999, "Biochemical and Electrophysiological Studies on the Mechanism of Action of PNU-151774E, A Novel Antiepileptic Compound," *Pharmacol. Exp. Ther*. 288:1151-1159.
Siderowf, A., 2001, "Parkinson's Disease: Clinical Features, Epidemiology, and Genetics," *Movement Disorders*, Aug, 19(3):565-578.
Stocchi, F. et al., 2006, Symptom Relief in Parkinson Disease by Safinamide: Biochemical and Clinical Evidence of Efficacy beyond MAO-B Inhibition; *Neurology* 67(7)SUPPL2:S24-S29.
Stocchi F. et al., 2004, "Improvement of Motor Function in Early Parkinson Disease by Safinamide," Neurology 63(4):746-748.
Sulkava, R. 2003, "Differential Diagnosis between Early Parkinson's Disease and Dementia with Lewy Bodies," *Adv. Neurol*, 91:411-413.
Summons to Attend Oral Hearings for European Patent Application 04 726 590.5-2123 dated Jul. 2, 2007.
Youdim, B. H. et al., 1991, "New Directions in Monoamine Oxidase A and B Selective Inhibitors and Substrates," *Biochem. Pharmacol*. 41(2): 155-162.
"AGILECT Improved Parkinson's Disease symptoms Without Worsening Cognitive and Behavioral Symptoms," *Pharmalive*, Oct. 27, 2004 (presented at Mental Dysfunction in Parkinson's Disease Conference), 3 pages.
Curatolo et al., "Neuroprotective Effects of Safinamide and its Methylated analogue in Rat Cortical Neurons," *Congresso Societa Italian NeuroScienze*, Torinio Sep. 8-11, 2001, 2 pages.
Maj et al., "Safmamide (NW-1015) is a novel combined MAO-B and glutamate release inhibitor with neuroprotective effects in animal models of Parkinson's Disease," *XXX Congresso Nazionale della Societa Italiana di Famacologia, Centro Congressi Magazzini del Cotone*, Genova, May 30-Jun. 2, 2001, *XXX Congresso SIF*, Poster No. B91, 5 pages.
Vaghi et al., "Neuroprotective Effect of PNU-151774E, A New Anticonvulsant Compound, in the Model of Global Ischaemia in Gerbils," *Ischemia: Ionic Mechanisms—Other/ABSTRACTS, Society for Neuroscience*, 27th Annual Meeting, New Orleans, LA, Oct. 25-30, 1997, 23, Part 1, 3 pages.
Chazot, 2001, "Safinamide Newron Pharmaceuticals," *Current Opinion in Investigational Drugs, Pharmapress, US*, 2(6):809-813.
Cattabeni, 2004, "Ralfinamide," *Idrugs, Current Drugs Ltd.*, 7(10):935-939.
Delumeau et al., 1994, "Monoamine oxidase inhibitors, cognitive functions and neurodegenerative diseases," *J. Neural Transm*, 41:259-266.
Pevarello, 1998, "Synthesis and Anticonvulsant Activity of a New Class of 2-[(Arylalkyl)amino]alkanamide Derivatives," *J. Med. Chem*., 41(4):579-590.
Youdim et al., 2005, "Multi-functional drugs for various CNS targets in the treatment of neurodegenerative disorders," *Trents in Pharmacological Sciences*, 26(1):27-35.
PCT International Search Report for PCT/EP2007/005197 dated Jan. 21, 2008.
Amendment filed Dec. 6, 2012 in co-pending U.S. Appl. No. 12/816,143.
Co-pending U.S. Appl. No. 12/816,143.

* cited by examiner

ALPHA-AMINOAMIDE DERIVATIVES USEFUL IN THE TREATMENT OF COGNITIVE DISORDERS

CROSS-REFERENCE TO RELATED APPLICATIONS

This is the §371 U.S. national stage of International Application No. PCT/EP2007/005197, filed Jun. 13, 2007, which claims the benefit of European patent application no. 06012352.8, filed Jun. 15, 2006, the disclosures of which are incorporated herein by reference in their entireties.

SUMMARY

The present invention relates to pharmacotherapy of cognitive disorders, i.e. deficits in learning and memory, by administering an α-aminoamide, particularly safinamide. Examples of disturbances in cognition that can be treated with the compound of the invention are those associated with disorders such as autism, dyslexia, attention deficit hyperactivity disorder, schizophrenia, obsessive compulsive disorders, psychosis, bipolar disorders, depression, Tourette's syndrome, Mild Cognitive Impairment (MCI) and disorders of learning in children, adolescents and adults, Age Associated Memory Impairment, Age Associated Cognitive Decline, Alzheimer's Disease, Parkinson's Disease, Down's Syndrome, traumatic brain injury Huntington's Disease, Progressive Supranuclear Palsy (PSP), HIV, stroke, vascular diseases, Pick's or Creutzfeldt-Jacob diseases, multiple sclerosis (MS), other white matter disorders and drug-induced cognitive worsening.

BACKGROUND OF THE INVENTION

Cognitive brain disorders are characterized clinically by progressive loss of memory, cognition, reasoning, executive functioning, planning, judgment and emotional stability, gradually leading to profound mental deterioration.

A wide range of disorders can lead to disturbances of cognition.

Neuropsychological cognitive deficits are common in people with functional neuropsychiatric disorders. Among these, schizophrenia is a chronic, severe and disabling form of psychosis. Scientists have estimated that up to 75% of schizophrenic patients are cognitively impaired. Traditional treatments for schizophrenia are not effective to treat cognitive deficits in schizophrenia, when used at high doses. While it has been reported that more recently developed treatments for schizophrenia, known as "atypical anti-psychotics," may have some effect on cognitive deficits, the effect may not be lasting or not lead to an improvement in daily functioning. There are currently no drugs approved for the treatment of cognitive deficits in schizophrenia.

More in general across several pathological conditions, with the increase of medical screening for dementia, an increasing number of patients are being identified who do not meet the diagnostic criteria for dementia but nonetheless have significant memory or cognitive impairment, defined as Mild Cognitive Impairment.

Mild Cognitive Impairment (MCI) is a condition characterized by mild recent memory loss without dementia or significant impairment of other cognitive functions to an extent that is beyond that expected for age or educational background. Criteria for diagnosis of MCI are: memory complaint; abnormal activities of daily living; abnormal general cognitive functioning; abnormal memory for age; not demented.

The number of patients falling in the categories of MCI, Age-Associated Memory Impairment, Age-Related Cognitive Decline or similar diagnostic categories is staggering. For example, according to the estimates of Barker et al. Br J Psychiatry, 1995 November; 167(5): 642-8, there are more than 16 million people with Age Associated Memory Impairment in the U.S. alone.

An advisory panel to the US Food and Drug Administration ruled on Mar. 13, 2001, that MCI, "a condition separate from dementia in Alzheimer's Disease (AD)," is a valid target for new drug therapies, regardless of whether a particular drug also slows the progression to dementia. However, so far the drugs that are being used in the treatment of this disease only have mild, temporary effects.

A variety of medications (including nonsteroidal anti-inflammatory drugs) hormones (especially estrogen), vitamins (e.g., vitamin E) and herbal preparations (especially *Gingko biloba*) have been advocated as treatments for memory loss. Acetylcholinesterase inhibitors, labelled for use in Alzheimer's disease, are also being tested for MCI. While some of these agents hold promise, robust effects from carefully executed, well-controlled clinical trials are still nonexistent. For all these reasons the unmet medical need in MCI is still very high.

Brain disorders characterized by cognition deficits are also those associated with progressive neuronal degeneration, or cell death secondary to trauma, infarction, hypoxia, infection or hydrocephalus and are characterized by memory impairment, but also other cognitive deficits with a pattern that lead to the diagnosis of dementia. Diseases associated with cognitive deficits and dementia are Alzheimer's Disease Parkinson's Disease, Huntington's Disease, HIV, vascular diseases, Pick's or Creutzfeldt-Jacob diseases, multiple sclerosis (MS), Progressive Supranuclear Palsy (PSP), and other white matter disorders. Among these diseases, Alzheimer's Disease represents the fourth most common medical cause of death in the United States. In 2005, Alzheimer's Disease was estimated to affect more than 4 million people in the United States, a number expected to increase within the next 20 years. A large number of drugs have been studied for their effect on improving the cognitive and behavioural aspects of Alzheimer's disease. The FDA has approved five drugs to treat Alzheimer's disease, but at best these drugs only provide mild relief, and do not attack the cause of AD. The five approved drugs for the treatment of AD are: tacrine, donezepil, rivastigmine, galantamine and memantine. Unfortunately these drugs cause only limited and time-depending benefit on cognitive deficits.

Parkinson's Disease (PD) is a chronically, progressive neurological disease, clinically characterized by motor disturbances, including rigidity, bradykinesia, gait disturbances postural instability, and tremor, which generally occurs during rest, but some patients have postural and action tremor components. The neurological hallmarks of PD are degeneration of dopamine neurons in substantia nigra pars compacta, which results in a drastic depletion of dopamine in the striatum, to which these neurons project. Cognitive impairment is also a characteristic of the disease, which occurs even in non-demented and early-stage PD patients and it is not strictly correlated to the motor symptoms of the disease.

It has been clearly recognised that in PD there are deficits related to attention, alertness, perception, motivation, intelligence and finally cognition and memory. These deficits in a large percentage of patients (roughly 50%), in particular in early PD patients, are not extensive and are not severe enough to be classified as dementia. Moreover in a high percentage of these patients the deficits do not progress to dementia. In some individuals cognitive decline can develop in the presence of mild Parkinson disease-related cortical pathology and, conversely, widespread cortical lesions do not necessarily lead to cognitive decline (Braak, H et al, Neurology, 64: 1404-1410, 2005).

At present the most widely used medication in PD is levodopa, which is still considered the golden standard, in spite of the severe motor complications that are evident after long term use of the drug. Since the early 1990s Dopamine Agonists (DA) have gained popularity, both as early therapy to delay the use of levodopa, and as adjunctive therapy to levodopa, when the efficacy of DA alone is not sufficient to control motor impairment of the patients.

Unfortunately, pharmacological intervention aimed at curing Parkinson's induced motor impairment, by restoring dopaminergic tone, not only do not substantially cure cognitive deficits, but very often have negative effects on cognition.

Evidences of no effect on cognition, or even impairment, are reported in the literature with levodopa. This negative findings are described by extensive literature. The following is a non exhaustive list:

Huber S J et al. Neurology, 1987 August; 37(8): 1371-5;
Huber S J et al. Neurology, 1989 March; 39(3): 438-40;
Poewe W et al., Ann Neurol. 1991 June; 29(6): 670-3;
Kulisevsky J et al., Brain, 1996 December; 119 (Pt 6): 2121-32;
Feigin A et al., Brain 2003 Jun. 10; 60(11): 1744).

Also the effects of Dopamine Agonists (DA), a widely prescribed class of compounds for treating PD, on cognition in Parkinson's patients, are often negative.

The effect of pergolide, a mixed D1/D2 agonist, on cognitive functions was evaluated in early-mild Parkinson's Disease (Brusa L et al., J Neural Transm. 2005 February; 112(2): 231-7). Cognitive assessment was performed after the washout phase and repeated after eight weeks (end of study) without showing amelioration of cognitive test scores.

In another cohort of mild PD patients pramipexole, a mixed D2/D3 agonist, slightly but significantly worsened verbal fluency, impaired short term verbal memory and attentional-executive functions in comparison to levodopa, although not exceeding normal values. (Brusa L et al., J Neural Transm. 2003, 110: 373-380).

Another dopaminergic drug, apomorphine, had a negative effect on reaction times, without influencing performance accuracy, in visual-spatial working memory (WM) (Costa A et al., Dement Geriatr Cogn Disord. 2003; 15(2): 55-66).

These data suggest that dopaminergic agents and in particular levodopa and dopamine agonists, whereas have proven efficacy in ameliorating motor function in PD patients, have controversial effects on cognition, even worsening some specific tasks.

On the other hand, a sizeable literature supports the hypothesis that cholinergic drugs may improve cognition, in particular in Alzheimer's Disease. More recently Emre M. et al. (New England Journal of Medicine, 2004, 351: 2509-2518) report the first large, multicentre comparison of a cholinesterase inhibitor (rivastigmine) in a double-blind, randomized placebo-controlled trial of patients with PD-related Dementia (PDD). Patients receiving rivastigmine responded better on the two primary outcome measures, Alzheimer's Disease Assessment Scale Cognitive Subscale and Clinical Global Impression of Change, as well as on all secondary outcome measures, including Neuropsychiatric Inventory, activities of daily living, executive functions and MMSE. The differences were moderate, however. More patients in the rivastigmine group (17%) dropped out due to adverse events than in the placebo group (8%), most commonly due to nausea. Even if objective assessment of parkinsonism did not differ between the groups, subjective worsening of tremor was reported more often in the rivastigmine (1.7%) than in the placebo arm, as expected by a drug acting on the cholinergic system. These data suggest that the above described pharmacological intervention can provide some benefit, but this is often obtained at the expenses of severe debilitating side effects, such as worsening in tremors. In fact Parkinson's disease tremor usually improves with anticholinergic medications. Anticholinergics include trihexyphenidyl, benztropine and procyclidine. However, the side effects of anticholinergic therapy, such as dry mouth, blurry vision, urinary difficulty, confusion and negative effects on cognition may limit the use of these agents.

All together these data show that cognitive impairment is still an area of high unmet medical need with no effective drugs. The moderate and inconsistent effect observed with some drugs, e.g. cholinesterase inhibitors, leave space to more effective and safe treatments. In particular in PD, where cholinesterase inhibitors cause worsening of tremors and interventions useful at restoring disease-related motor impairment, such as levodopa or DA, often worsen cognitive functions, the need of new drugs that ameliorate cognition without worsening the motor disturbancies of the disease, is very high.

DETAILED DESCRIPTION OF THE INVENTION

In accordance to this invention it has been found that α-aminoamide compounds of the formula (I) and their pharmaceutically acceptable salts, in particular safinamide, are effective in treating cognitive disorders that are observed in the above variety of diseases and can be administered orally without the toxic side effects caused, for example, by anticholinesterase activity associated with compounds such as phenserine, rivastigmine, donezepil and galanthamine.

α-aminoamide compounds of the formula (I) and in particular safinamide, are not cholinesterase inhibitors. Therefore toxic effects such as nausea, vomiting, dizziness, bradychardia, increase in tremor, such as the one observed with rivastigmine in PD patients (Emre M. et al. NEJM, 351, 2509-2518, 2004) are not expected after administration of α-aminoamide compounds of the formula (I) and in particular safinamide.

Safinamide is instead a selective MAO-B inhibitor (devoid of activity on MAO-A) and glutamate release inhibitor in condition of pathological glutamate overflow. Safinamide is not a glutamate receptor antagonist as it has no affinity for any of the glutamate receptors. Its mechanism of action is described in several publication of which the following is a non exhaustive list:

Biochemical and Electrophysiological Studies on the Mechanism of Action of PNU-151774E, a Novel Antiepileptic Compound; Salvati P. et al. J. Pharmac. Exp. Ther.; 288: 1151-1159, March 1999.

Characterization of MAO-B inhibitory properties of Safinamide (NW-1015) in animals models and healthy volunteers. C. Caccia et al. Abs 862.16—31st Annual Meeting Society for Neuroscience 2001 San Diego, Calif., Nov. 10-15.

Neuroprotective effects of safinamide and its methylated analogue in rat cortical neurons. Curatolo L., et al. Poster G-36—Congresso Nazionale SINS—Torino, 8-11 Settembre 2001.

Safinamide (NW-1015) is a novel combined MAO-B and glutamate release inhibitor with neuroprotective effects in animal models of Parkinson's Disease. R. Maj et al. Poster n. B91—XXX Congresso Nazionale SIF Genova, 30 Maggio-2 Giugno 2001.

It has also been suggested that safinamide might have long term neuroprotective effects in addition to symptomatic effects in neurodegenerative disorders and in particular PD and ischemia. This effect has been demonstrated in animal models (F. Vaghi et al; 27 th annual meeting Neuroscience New Orleans 1997 Oct. 25-30 abs n 212.9). However it has been shown (Journal of Pharmacology and Experimental Therapeutics, 1998, 285: 397-403) that safinamide "per se" does not ameliorate cognition in the rat passive avoidance test in normal rats, a test in which nootropic agents, which are claimed to ameliorate cognition in humans, are active.

Clinical data in PD patients have shown that safinamide significantly ameliorated UPDRS scores after 3 month treatment. The improvement is particularly evident when safinamide is associated to a dopamine agonist (Stocchi, F et al. Neurology, 2004 Aug. 24; 63(4): 746-8).

We have now unexpectedly discovered that in a six month double blind clinical trial in non demented patients with early PD, safinamide associated to a dopamine agonist (DA) is able not only to significantly ameliorate UPDRS scores, which are related to the motor symptoms of the disease, as compared to the group treated with the DA alone (control group), but also to ameliorate cognitive worsening observed in controls and/or improve cognition as compared to pretreatment, at the check of both three and six months after start of treatment. More in detail what was surprisingly found was that safinamide added to a stable dose of a DA, was able of: a) counteracting the worsening in cognition observed with the DA alone as compared to baseline (a worsening that is in line with what described in the literature above quoted); b) ameliorating the performance of patients in a series of tests as compared to the baseline performance observed before treatment start.

This is a novel finding as previous disclosures have associated compounds of the formula (1) to degenerative diseases and in particular PD and ischemia, where the neuroprotectant role of the compounds and safinamide in particular, due to their MAO-B inhibitory activity and anticonvulsant activity would play a role and cause disease modifying effects. The compounds of the formula (1) claimed in WO 90/14334 were shown to inhibit convulsions and lethality caused by bicuculline and mercaptopropionic acid and inhibit MAO activity. It was already suggested at the time of that disclosure that MAO-B inhibitors might have a neuroprotectant effects (Strolin Benedetti M and Doster P, Biochem. Pharmacol. 1988, 38, 555-561).

The mechanism by which safinamide causes a positive effect on cognition observed in the present invention is not elucidated. It is however very unlikely that a neuroprotective effect, such as the one described for safinamide in animal models, would be measurable in only 12 weeks, a relatively too short period of time, and neuronal cell death is not reversible. What is expected by a neuroprotectant agent is to possibly slow down disease progression, and in long term trials (such as two year trials) demonstrate that the worsening observed in control patients is attenuated significantly by drug treatment.

So, as compared to previous disclosures, this effect, which becomes apparent in such a short time, is completely unexpected.

A wide range of relatively subtle cognitive deficits can be observed in patients with Parkinson's disease (PD). Deficits have been recognized in different cognitive domains such as memory, visuospatial processing, attention, concept formation, and executive functions.

The similarities of some cognitive deficits to those reported following focal lesions of the prefrontal cortex, together with dopamine's role in the modulation of complex circuits linking the basal ganglia with prefrontal cortex, have led to the hypothesis that changes in the levels of dopamine stimulation may modify cognitive performance.

However, in patients with PD both levodopa and dopamine agonists has been reported to improve, impair, or not affect frontal cognitive performance, and to improve, impair, or not affect memory functions as above reported.

These data suggest that levodopa and dopamine agonists, whereas have proven efficacy in ameliorating motor function in PD patients, have controversial effects on cognition, even worsening some specific tasks. The reason for these discrepancies might reside on the fact that excessive dopamine receptor stimulation can be detrimental to cognitive function (Murphy B L, et al, PNAS, 1996, vol 93 and Ruzicka E et al., J Neurol. Neurosurg. Psychiatry, 57, 998-1001, 1994). It has been suggested that there might be a critical range of dopaminergic activity for optimal cognitive functioning and that exceeding this range might result in dysregulation of cognition.

The effects of MAO-B inhibitors on cognitive functions have been suggested to be mainly related to their neuroprotectant effect, but also it has been hypothesized that it might be due to an increase availability of neurotransmitters, and in particular dopamine, in relevant brain areas. Shortage of dopamine has been in fact suggested to be involved in the pathophysiology of memory impairment in PD patients (J Neural Transm. (1994) 41: 259-266; Trends in Pharmacological Sciences, (2005) 26: 27-35).

However, rasagiline a MAO-B inhibitor used in PD therapy, was reported not to ameliorate cognition, but simply not to worsen it:—"rasagiline, 1 mg dose once daily, improved symptoms of PD, including motor fluctuations, without significantly increasing the occurrence of cognitive and behavioural adverse events in early and moderate-to-advanced PD patients"—as quoted from re-analysis of TEMPO and PRESTO pivotal studies on Agilet (rasagiline), presented at the "Mental Dysfunction in Parkinson's Disease Conference, Salzburg, Austria, 2004.

So again what may be critical is the optimal tuning of different mediators and dopamine in particular selected brain areas. Unexpectedly safinamide ameliorated cognition in association with a dopamine agonist, that per se in the present trial caused a worsening of some cognitive functions, in line with the above quoted literature.

This cannot be due to its MAO-B inhibitory effect. This in fact would naturally cause an increase in dopamine availability and we might be quite sure that this happened considering that in the same trial safinamide ameliorated the motor score (UPDRS) over the effect of the dopamine agonist and UPDRS is strictly related with the dopaminergic tone. In fact we can suggest that the worsening observed in DA agonist treated patient might be due to an already high level of dopaminergic stimulation in the prefrontal cortex over the optimal level that is suggested to ameliorate cognition. Nevertheless when added to this DA agonist regiment safinamide was able to revert the impairment. This is totally unexpected for a MAO-B inhibitor.

In addition, also the glutamate release inhibitory effect of safinamide cannot explain the present positive findings on cognitive functions of PD patients.

Glutamate is the main excitatory neurotransmitter in the mammalian CNS and mediates neurotransmission across most excitatory synapses. Glutamate stimulates a number of postsynaptic receptors including NMDA and AMPA receptors.

As supported by a large bulk of literature evidence, reduction of glutamate receptors activity, and in particular NMDA receptors, clearly disrupts learning and memory. And in fact NMDA and AMPA receptor agonists (not antagonists) have been studied for their potential of enhancing cognition (Weiser T, 2004, in Cognitive enhancing drugs" Buccafusco J J editor, pp 89-96—Birkhauser, Austria).

It is somehow curious therefore, that an NMDA receptor antagonist, memantine, was the first glutamatergic drug to reach the clinical scene for cognition and AD. This example, and its peculiarity, is specifically mentioned by Youdim M B and Buccafusco J J, Trends in Pharmacological sciences (2005) 26: 27-35). Memantine is currently approved in US for the treatment of moderate to severe AD. One hypothesis is that this effect can be linked to the neuroprotective action of the drug. Another hypothesis is that glutamate receptors of the NMDA type are over-activated in a tonic rather than a phasic manner in AD. This continuous mild activation may lead to neuronal damage and impairment of synaptic plasticity (learning). It is likely that under such conditions Mg 2+ ions, which block NMDA-gated channel under normal resting conditions, cannot longer do so. One hypothesis is that memantine is a glutamate antagonists with features of "improved magnesium" as it mimics Mg2+ and attenuates this deficit and restores synaptic plasticity by taking over the physiological role of Mg2+ (Danysz W and Parsons C G.; Int J Geriatr Psychiatry (2003) 18(Suppl 1): S23-32; Danysz W, Parsons C G, Mobius H J, Stoffler A, Quack G.; *Neurotox Res*. (2000) 2(2-3): 85-97).

If this hypothesis is true, it relates the activity of an NMDA antagonist as cognitive enhancer to a specific mechanism of action, linked to the Mg2+ binding site. This does not generally applies to all NMDA antagonists, that, as above reported, generally negatively affect cognition, nor to a compound, like safinamide, that inhibit glutamate release and do not act via the glutamate receptors.

One drug described to be a glutamate release inhibitor is riluzole. In preclinical testing this compound has been shown to improve cognition for example following experimental brain injury in the rat, but its effect was likely mediated by a neuroprotective mechanism. And in fact the compound has been shown to be neuroprotective also in models of cerebral ischemia and PD (Benazzouz A et al., Eur. J. of Pharmacol. 1995, 284, 299-307; J Neurotrauma, 1996, 13, 767-80).

Riluzole, approved for ALS in the US in 1996, is in clinical trials for PD and AD, but the rationale of these trials is based on its neuroprotectant effect.

For all these reasons there is not a clear cut relationship between the mechanisms of actions of safinamide and its positive effects on cognition observed in association with a DA that per se caused an impairment on the cognitive function, as demonstrated in the present invention. This is particularly true considering that neuroprotection, that is the mechanism more likely associated to a positive effect on cognition caused by MAO-B inhibitors or the NMDA antagonist memantine, or riluzole, cannot be advocated, due to the short duration of the trial herein described. Nor it can be advocated its possible ehancing effect of dopamine levels in relevant CNS areas, due to MAO-B inhibition, as safinamide was not given in monotherapy but associated to a DA that "per se" already caused an impairment on cognition likely due to dopaminergic over stimulation.

Finally, it is important to mention that memory is represented by several distinct processes and different types of memory are associated with different brain regions. For these reasons many neurotransmitter substances are involved in cognition, including acetylcholine, noradrenaline, dopamine, serotonin, GABA, glutamate, histamine, peptides, and their receptors. These mediators works together, but due to modulation of one system on the other, sometimes the combined activity on more than one target might be unpredictable. Practical applications of combining agents with different therapeutic targets are not prevalent in the literature.

More specifically there is no example in the literature, to our knowledge, of compounds with a MAO-B inhibitory activity associated to glutamate release inhibitory effect and no examples that such a drug should have a positive effect on cognition.

From the lack of previous demonstration that such association of mechanisms is indeed positive for cognition, the present finding is unexpected.

In addition to the beneficial effects on both motor and cognitive aspects of the disease, the safety profile of safinamide, in combination with the DA, was extremely favourable. This represent a further therapeutic advantage of the present invention, considering that cholinesterase inhibitors, which proved a moderate beneficial effect in ameliorating cognition deficit in PD patients, worsen some aspects of motor performance and cause a variety of unwanted side effects. One embodiment of the present invention is that safinamide, or more in general a compound of the formula (I), is useful in preventing or ameliorating the negative effect caused by a dopamine agonist on cognitive performance of a PD patient.

Considering the marked effect observed in association with a DA, and considering that all treatments in PD cause an increase of dopaminergic tone, one embodiment of the present invention is that safinamide, and more in general compounds of the formula (I), are useful for treating cognitive impairment associated with the use of levodopa and other medicaments used for treating PD.

More in general the present invention provides a rapid and highly effective method, superior to existing treatments, for treating cognitive disorders by utilizing an α-aminoamide compound of the general formula (I).

It has been found that α-aminoamide compounds of the formula (I) and in particular safinamide, are able of improving Cognitive Function and Treating Cognitive Impairment in a mammal (e.g., human, non human primate or rat). Improving cognitive function includes "promoting" cognitive function (affecting impaired cognitive function in the subject so that it more closely resembles the function of an aged-matched normal, unimpaired subject, including affecting states in which cognitive function is reduced compared to a normal subject) and "preserving" cognitive function (affecting normal or impaired cognitive function such that it does not decline or does not fall below that observed in the subject upon first presentation or diagnosis, e.g., to the extent of expected decline in the absence of treatment). In one embodiment of the invention, the mammal has normal cognitive function which is improved. In one embodiment the mammal exhibits cognitive impairment associated with aging. In one embodiment the mammal is a human with cognitive impairment associated with a disease or disorder. In one embodiment the mammal is a human exhibiting cognitive function impairment associated with disorders such as autism, dyslexia, attention deficit hyperactivity disorder, schizophrenia, obsessive compulsive disorders, psychosis, bipolar disorders, depression, Tourette's syndrome and disorders of learning in children, adolescents and adults, Age Associated Memory Impairment, Age Associated Cognitive Decline, Parkinson's Disease, Down's Syndrome, traumatic brain injury Huntington's Disease, Progressive Supranuclear Palsy (PSP), HIV, stroke, vascular diseases, Pick's or Creutzfeldt-Jacob diseases, multiple sclerosis (MS), other white matter disorders and drug-induced cognitive worsening. In one embodiment, the impairment of cognitive function is caused by, or attributed to, Alzheimer's disease. In another embodiment, the impairment of cognitive function is caused by, or attributed to, mild cognitive impairment (MCI).

The invention concerns the use of compounds of formula (I)

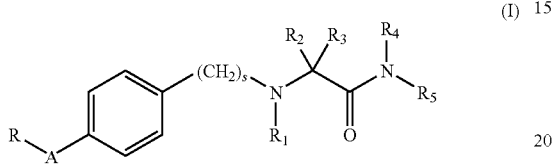

wherein:
A is a $(CH_2)_n$—X group, wherein n is an integer from 0 to 5, X is $CH_2$, O, S or NH;
s is 1 or 2;
R is a furyl, thienyl, pyridyl or a phenyl ring, optionally substituted by one or two substituents independently selected from halogen, hydroxy, cyano, $C_1$-$C_6$ alkyl, $C_1$-$C_6$ alkoxy or trifluoromethyl;
$R_1$ is hydrogen, $C_1$-$C_6$ alkyl or $C_3$-$C_7$ cycloalkyl;
$R_2$ and $R_3$ are independently selected from hydrogen; $C_1$-$C_4$ alkyl, optionally substituted by hydroxyl, phenyl, phenyl, optionally substituted by one or two substituents independently selected from $C_1$-$C_6$ alkyl, halogen, hydroxy, $C_1$-$C_6$ alkoxy or trifluoromethyl or $R_2$ and $R_3$, taken with the carbon atom which they are linked to, form a $C_3$-$C_6$ cycloalkyl ring;
$R_4$, $R_5$ are, independently, hydrogen, $C_1$-$C_6$ alkyl, $C_3$-$C_7$ cycloalkyl or $R_4$ and $R_5$, taken together with the nitrogen atom they are linked to, form a 5-7 atom saturated heterocyclic ring;
or isomers, mixtures, and pharmaceutically acceptable salts thereof for the preparation of a medicament for the for improving Cognitive Function and treating Cognitive Impairment.

The alkyl and alkoxy groups can be branched or can be straight chain groups.

Pharmaceutically acceptable salts of the compounds of the invention include, for example, acid addition salts with inorganic acids, e.g., nitric, hydrochloric, hydrobromic, sulfuric and phosphoric acids and the like, or organic acids, e.g., acetic, propionic, glycolic, lactic, oxalic, malonic, malic, tartaric, citric, succinic, benzoic, cinnamic, mandelic, methanesulfonic, p-toluenesulfonic and salicylic acids, and the like.

Some of the compounds of formula (I) can have asymmetric carbon atoms, and therefore, can exist either as racemic mixtures or as individual optical isomers (enantiomers). Accordingly, the term "pharmaceutically acceptable salts" of the α-aminoamide of formula (I) is also meant to include within its scope all the possible isomers and their mixtures, and any pharmaceutically acceptable metabolite, bioprecursor and/or pro-drug, i.e., a compound which has a structural formula different from the one of the the α-aminoamide of formula (I), and yet is directly or indirectly converted in vivo into a compound having formula (I), upon administration to a mammal, particularly a human being.

Preferred compounds of formula (I) are those wherein A is a group chosen from $CH_2$, $(CH_2)_2$, $CH_2$—S, and $(CH_2)_n$—O, wherein n is an integer from 1 to 5;
s is 1 or 2;
R is a phenyl ring, optionally substituted by one or two substituents independently selected from halogen, trifluoromethyl, methoxy, or a thienyl ring;
$R_1$ is hydrogen or $C_1$-$C_4$ alkyl;
$R_2$ and $R_3$ are independently hydrogen or $C_1$-$C_4$ alkyl, optionally substituted by hydroxy or phenyl, optionally substituted by one or two halogen atoms, or $R_2$ and $R_3$ form with the atom they are linked to a $C_1$-$C_6$ cycloalkyl ring;
$R_4$, $R_5$ are hydrogen or $C_1$-$C_4$ alkyl or, together with the nitrogen atom they are linked to, form a pyrrolidine or a piperidine ring, and the pharmaceutically acceptable salts thereof.

Examples of specific compounds of formula (I), include:
2-(4-Benzyloxybenzylamino)-propanamide;
2-[4-(2-Methoxybenzyloxy)-benzylamino]-propanamide;
2-[4-(2-Fluorobenzyloxy)-benzylamino]-propanamide;
(S)-(+)-2-[4-(2-Fluorobenzyloxy)-benzylamino]-propanamide;
(R)-(−)-2-[4-(2-Fluorobenzyloxy)-benzylamino]-propanamide;
2-[4-(2-Fluorobenzyloxy)-benzylamino]-2-methyl-propanamide;
2-[4-(2-Fluorobenzyloxy)-benzylamino]-N-methyl-propanamide;
N-{2-[4-(2-Fluorobenzyloxy)-benzylamino]}-propionyl-pyrrolidine;
2-[4-(3-Methoxybenzyloxy)-benzylamino]-propanamide;
2-[4-(3-Cyanobenzyloxy)-benzylamino]-propanamide;
2-[4-(3-Fluorobenzyloxy)-benzylamino]-propanamide;
(S)-(+)-2-[4-(3-Fluorobenzyloxy)-benzylamino]-propanamide;
(R)-(−)-2-[4-(3-Fluorobenzyloxy)-benzylamino]-propanamide;
2-[4-(3-Fluorobenzyloxy)-benzylamino]-2-methyl-propanamide;
2-[4-(3-Fluorobenzyloxy)-benzylamino]-N-methyl-propanamide;
N-{2-[4-(3-Fluorobenzyloxy)-benzylamino]}-propionyl-pyrrolidine;
2-[4-(4-Fluorobenzyloxy)-benzylamino]-propanamide;
2-[4-(3-Fluorobenzyloxy)-benzylamino]-2-methyl-propanamide;
2-[4-(2-Chlorobenzyloxy)-benzylamino]-propanamide;
(S)-(+)-2-[4-(2-Chlorobenzyloxy)-benzylamino]-propanamide;
(R)-(−)-2-[4-(2-Chlorobenzyloxy)-benzylamino]-propanamide;
2-[4-(3-Chlorobenzyloxy)-benzylamino]-propanamide;
(S)-(+)-2-[4-(3-Chlorobenzyloxy)-benzylamino]-propanamide;
(R)-(−)-2-[4-(3-Chlorobenzyloxy)-benzylamino]-propanamide;
2-(4-Benzyloxybenzylamino)-3-hydroxy-propanamide;
2-[4-(2-Fluorobenzyloxy)-benzylamino]-3-hydroxy-propanamide;
2-[4-(3-Fluorobenzyloxy)-benzylamino]-3-hydroxy-propanamide;
2-(4-Benzyloxybenzylamino)-3-hydroxy-N-methyl-propanamide;
2-[4-(2-Fluorobenzyloxy)-benzylamino]-3-hydroxy-N-methyl-propanamide;

2-[4-(3-Fluorobenzyloxy)-benzylamino]-3-hydroxy-N-methyl-propanamide;
2-[4-(2-Chlorobenzyloxy)-benzylamino]-3-hydroxy-N-methyl-propanamide;
2-[4-(3-Cyanobenzyloxy)-benzylamino]-3-hydroxy-N-methyl-propanamide;
2-[4-(3-Cyanobenzyloxy)-benzylamino]-2-methyl-3-hydroxy-N-methyl-propanamide;
2-[4-(2-Fluorobenzyloxy)-phenylethylamino]-propanamide;
2-[4-(3-Fluorobenzyloxy)-phenylethyl amino]-propanamide;
2-[4-(2-Chlorobenzyloxy)-phenylethylamino]-propanamide;
2-[4-(3-Chlorobenzyloxy)-phenylethylamino]-propanamide
2-{4-[2-(3-Fluorophenyl)-ethoxy]benzylamino}-propanamide;
2-{4-[2-(3-Fluorophenyl)-ethyl]benzylamino}-propanamide;
2-[N-(4-Benzyloxybenzyl)-N-methylamino]-propanamide;
2-[4-Benzylthiobenzylamino]-propanamide;
2-[4-(2-Fluorobenzylthio)-benzylamino]-propanamide;
2-[4-(2-Chlorobenzylthio)-benzylamino]-propanamide;
2-[4-(3-Fluorobenzylthio)-benzylamino]-propanamide;
2-[4-(3-Chlorobenzylthio)-benzylamino]-propanamide;
2-[4-(3-Phenylpropoxy)-benzylamino]-propanamide;
2-[4-(4-Phenylbutoxy)-benzylamino]-propanamide;
2-[4-(5-Phenylpentoxy)-benzylamino]-propanamide;
2-(4-Benzyloxybenzylamino)-3-phenyl-N-methyl-propanamide;
2-(4-Benzyloxybenzylamino)-3-methyl-N-methyl-butanamide;
2-(4-Benzyloxybenzylamino)-2-phenyl-acetamide;
2-[4-(2-Fluorobenzyloxy)-benzylamino]-2-phenyl-acetamide;
2-[4-(3-Fluorobenzyloxy)-benzylamino]-2-phenyl-acetamide;
2-[4-(2-Fluorobenzyloxy)-benzyl-N-methylamino]-2-phenyl-acetamide;
2-[4-(3-Fluorobenzyloxy)-benzyl-N-methylamino]-2-phenyl-acetamide;
2-[4-(3-Chlorobenzyloxy)-benzylamino]-2-phenyl-acetamide;
2-[4-(2-Fluorobenzyloxy)-benzylamino]-2-(2-fluorophenyl)-acetamide;
2-[4-(2-Fluorobenzyloxy)-benzylamino]-2-(3-fluorophenyl)-acetamide;
2-[4-(3-Fluorobenzyloxy)-benzylamino]-2-(2-fluorophenyl)-acetamide;
2-[4-(3-Fluorobenzyloxy)-benzylamino]-2-(3-fluorophenyl)-acetamide;
2-[4-(3-Chlorobenzyloxy)-benzylamino]-2-(3-fluorophenyl)-acetamide;
2-(4-(2-Thienyloxy)-benzylamino)-propanamide;
or isomers, mixtures, and pharmaceutically acceptable salts thereof.

Preferred compounds of formula (I), which can be used as monotherapy, or in combination with other compounds of formula (I), in an effective amount for treating one or more cognitive disorder in a patient, are: (S)-(+)-2-[4-(2-fluorobenzyloxy)-benzylamino]-propanamide or (S)-(+)-2-[4-(3-fluorobenzyloxy)-benzylamino]-propanamide.

Compounds of formula I are known from WO90/14334, WO94/22808, WO97/05102, WO 97/05111, WO 99/35123 and WO99/035125 as compounds active on the central nervous system and useful as anti-epileptic, anti-Parkinson, neuroprotective, antidepressant, and antispastic hypnotic agents (see also Pevarello P. et al. (1998), J. Med. Chemistry, 41: 579-590).

In one embodiment the patient being treated is a mammal, including humans, in need of alleviation, or inhibition of symptoms of cognitive disorders.

Specific examples of cognitive disorders are autism, dyslexia, attention deficit hyperactivity disorder, anxiety, schizophrenia, obsessive compulsive disorders, psychosis, bipolar disorders, Tourette's syndrome, Mild Cognitive Impairment (MCI) and disorders of learning in children, adolescents and adults, Age Associated Memory Impairment, Age Associated Cognitive Decline, Down's Syndrome, HIV, vascular diseases.

Particularly, the mammal in need of the above mentioned treatment is administered a dose of an α-aminoamide of formula (I) as above defined which ranges from about 0.3 to about 100 mg/kg of body weight per day. "Treatment" as used herein includes any care by procedures or applications to a mammal, and particularly a human, that are intended to: a) prevent the disease or disorder from occurring in a subject that may be predisposed to the disease/disorder, but has not yet been diagnosed with having it; b) inhibiting the disease/disorder, or condition, i.e., arresting its development; c) relieving the disease/disorder, or condition, i.e., causing regression of the disease/disorder, or condition.

Cognitive disorders condition in a mammal, including humans, can thus be inhibited or alleviated.

In another aspect, the invention includes an α-aminoamide of formula (I) administered as the active agent of a pharmaceutically acceptable composition having activity in the treatment of cognitive disorders which can be prepared by conventional procedures, for instance by mixing the active agent with a pharmaceutically acceptable, therapeutically inert organic and/or inorganic carrier or excipient materials.

In one embodiment of the invention, the mammal has cognitive function which is further deteriorated by the administration of a drug used to treat PD. In that case the compound is given in combination with such agent. Combination therapy (or "co-therapy") includes the administration of an α-aminoamide compound of formula (I) of the invention and at least a second agent, for example:

dopamine agonists such as bromocriptine, cabergoline, lisuride, pergolide, ropinirole, apomorphine, sumanirole, rotigotine, talipexole, dihydroergocriptine and pramipexole, levodopa, levodopa plus carbidopa (SINEMET®), levodopa plus controlled release carbidopa (SINEMET-CR®), levodopa plus benserazide (MADOPAR®), levodopa plus controlled release benserazide (MADOPAR-HBS), COMT inhibitors such as tolcapone and entacapone, STALEVO®, Amantadine, as part of a specific treatment regimen intended to provide the beneficial effect by counteracting the negative effects on cognition of the above mentioned agents (alone or in different combination) and at the same time further ameliorate motor dysfunction in PD.

One embodiment of the present invention is the association of the compound of the formula (I), and in particular safinamide, with anticholinergic agents that are used in PD for treating tremors. In fact Parkinson's disease tremor usually improves with anticholinergic medications. Anticholinergics include trihexyphenidyl, benztropine, and procyclidine. However, the side effects of anticholinergic therapy are numerous and include negative effects on cognitive functions.

The compounds of the present invention are also useful in association with other drugs, such as cholinesterase inhibitors and/or acetylcholine modulators, but not limited to, that are useful in improving cognitive function in pathological conditions such as Alzheimer's Disease, PD and all conditions above mentioned.

Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations contemplated by the present invention. "Combination therapy" is intended to embrace administration of these therapeutic agents in a sequential manner or simultaneously. Simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally.

Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the combination of the therapeutic agents and non-drug treatment is achieved.

The α-aminoamide compositions of the invention can be administered in a variety of dosage forms, e.g., orally, in the form of tablets, troches, capsules, sugar or film coated tablets, liquid solutions, emulsions or suspensions; rectally, in the form of suppositories; parenterally, e.g., by intramuscular or intravenous injection or infusion; and transdermally in the form of a patch, ointment, emulsion, lotion, solution, gel, cream, aerosol and nasal spray.

Suitable pharmaceutically acceptable, therapeutically inert organic and/or inorganic carrier or excipient materials useful in the preparation of such composition include, for example, water, gelatin, gum arabic, lactose, starch, cellulose, magnesium stearate, talc, vegetable oils, cyclodextrins, polyalkyleneglycols and the like. The α-aminoamide compositions of formula (I) can be sterilized and may contain further components, well known to those skilled in the art, such as, for example, preservatives, stabilizers, wetting or emulsifying agents, e.g., paraffin oil, mannide monooleate, salts to adjust osmotic pressure, buffers and the like.

Additionally, the solid oral forms can contain, together with the active agent, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gums, gelatin, methylcellulose, carboxymethylcellulose or polyvinyl pyrrolidone; disaggregating agents, e.g., a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. The pharmaceutical preparations may be manufactured in any known manner, for example, by means of mixing, granulating, tabletting, sugar-coating, or film-coating processes.

The oral formulations comprise sustained release formulations which can be prepared in a conventional manner, for instance by applying an enteric coating to tablets and granules.

The liquid dispersion for oral administration may be e.g., syrups, emulsions and suspension. The syrups may further contain as a carrier, for example, saccharose or saccharose with glycerine and/or mannitol and/or sorbitol.

Suspensions and emulsions may contain as a carrier, for example, a natural gum, agar, sodium alginate, pectin, methylcellulose, carboxymethyl-cellulose, or polyvinyl alcohol. The suspensions or solutions for intramuscular injections may contain, together with the active compound, a pharmaceutically acceptable carrier, e.g., sterile water, olive oil, ethyl oleate, glycols, e.g., propylene glycol, and, if desired, a suitable amount of lidocaine hydrochloride. The solutions for intravenous injections or infusion may contain as a carrier, for example, sterile water or preferably they may be in the form of sterile, aqueous, or isotonic saline solutions.

The suppositories may contain, together with the active agent, a pharmaceutically acceptable carrier, e.g., cocoa butter, polyethylene glycol, a polyoxyethylene sorbitan fatty acid ester surfactant or lecithin.

Compositions including α-aminoamides of formula (I) are generally in the form of a dose unit containing, for example, 20 to 7000 mg of active ingredient per unit dosage form. Suitable treatment is given 1 or 2 or 3 times daily, depending upon clearance rate. Accordingly, the desired dose may be presented in a single dose or as divided doses administered at appropriate intervals, for example, two to four or more sub-doses per day.

The pharmaceutical compositions including an α-aminoamide of formula (I) can contain, per dosage unit, e.g., capsule, tablet, powder injection, teaspoonful, suppository and the like, from about 20 to 7000 mg of the active agent.

Optimal therapeutically effective doses to be administered may be readily determined by those skilled in the art and will vary, basically, with the strength of the preparation, with the mode of administration and with the advancement of the pathological condition or the specific memory or cognition disorder treated. In addition, factors associated with the particular subject being treated, including subject age, weight, diet and time of administration, will result in the need to adjust the dose to an appropriate therapeutically effective level.

The advantages derived from the uses and the methods of the invention as above defined are many, and include the possibility to treat basically all types of cognitive disorders symptoms, with a surprisingly favourable profile of safety.

EXAMPLES

Clinical Examples

Example 1: The Cogtest

Cogtest® (Computerized Cognitive Test Battery for Clinical Trials) is designed to provide with the highest quality computerised cognitive tests for use in clinical trials. All cognitive tests in the Cogtest® battery have been developed by academic neuropsychologists and clinical trials specialists. This ensures that the most recent developments in cognitive neuroscience, including neurophysiological, functioning neuroimaging and pharmacogenic evidence are incorporated into the Cogtest® library of procedures and into pharmaceutical clinical trials.

The Cogtest PD battery has been prepared, based on a review of the available tests in the Cogtest library and selection of those tests that would most usefully comprise a battery suitable for Parkinson's Disease. However the same tasks are used in other pathological conditions for testing the two main domains of cognition, reaction time and power.

The battery takes from 20-30 minutes to administer, and is applicable across different cultures and countries. The following tests were included in the battery:

Test 1—Auditory Number Sequencing

The Auditory Number Sequencing task is a test of working memory and executive function. The participant will be presented with clusters of numbers (e.g. 936) of increasing length (from 2 digits to a maximum of 8 digits). They will be asked to tell the tester the numbers in order, from lowest to highest. This task has been adapted from the original Cooper Digit Ordering Task (Cooper J A et al. (1991), Brain, 114: 2095-2122) which has been shown to be sensitive to pharmacological interventions, for example in PD patients (Cooper J A et al. (1992) Brain, 115, 1701-1725; Cooper J A et al. (1993), Neuropsychologia, 31, 933-949; Gabrieli J D E et al., (1996), Neuropsychology, 10, 322-332; Hoppe C et al., (2000). The Clinical Neuropsychologist, 14, 38-55)

Test 2—Spatial Working Memory (SWM)

The overall goal of the task is to determine how accurately subjects recall the spatial locations of briefly presented visual targets. The task involves showing the targets at various positions on a display device, and having subjects touch the screen at the location where they recall the target had appeared. After instructions, there are 2 conditions: (1) Direct Touching of the targets while they are still on the screen; (2) Delay condition, where there is a delay between target presentation and the opportunity to respond, with equal numbers of trials (randomized) involving either 2 second or 12 second delay between target presentation and the opportunity to respond. During the delay between presentation and recall, a number of distracters of variable location appear that need to be actively touched by the subject. The distracter condition helps prevent both the subject's visual fixation location and hand position from remaining near the target.

Test 3—Strategic Target Detection (STD)

This test is similar to the paper-and-pencil 'cancellation' tests or the cross-out' subtest of the WAIS-III, where subjects are required to crossout target stimuli embedded among distracters. In this computerized test, the participant touches the target stimuli (shapes) directly on the touch screen. An added feature of this test is that the subject is not told in advance which of the stimuli is the 'target'. Instead, the subject must learn which is the correct target by choosing one of the stimuli and observing feedback that indicates whether the choice was right or wrong. This feature is similar to that used in the Wisconsin Card Sorting Test (WCST), where the correct 'rule' is learned by subjects only from examiner feedback. The variables measured are: Total Experiment Time (from the end of the 'Get ready' screen to the end of the last response, in msec), Total Correct responses, Total Perseverative Errors (erroneous pressing of the shape that was the target of the last set, but is not for this set), Strategic efficiency variable (the cumulative distance of territory transversed, i.e., between the location of correct presses on screen for each set) according to literature (Weintraub, S., & Mesulam, M. M. (1987). Archives of Neurology 44 621-625).

Test 4—Tapping Speed

The tapping speed test assesses simple motor speed and manual dexterity. The Cogtest version is similar to the Finger Tapping Test or Finger Oscillation Test of the Halstead Reitan Neuropsychological Battery, which has been extensively used in many neuropsychological studies and is sensitive to the motor effects of antipsychotics and to the effects of many neurological illnesses (including cerebrovascular and Parkinson's diseases) in which it shows good sensitivity to lateralized brain dysfunction. In addition to capturing the total number of taps with the index finger of each hand, it also captures the latency to each and every response, generating an index of the variance in tapping speed.

The summary variables are: Mean Tap Rate per trial (Right hand) (the mean inter-tap interval in msec), Standard Deviation Tap Rate over all trials (Right hand) (the mean inter-tap interval in msec), Total taps (Right hand), Mean Tap Rate per trial (Left hand) (the mean inter-tap interval in msec), Standard Deviation Tap Rate over all trials (Left hand) (the mean inter-tap interval in msec), Total taps (Left hand), according to literature (Reitan, R. M. (1979) Manual for administration of neuropsychological test batteries for adults and children. Tucson, Ariz.: Reitan Neuropsychology Laboratories, Inc.; Reitan, R. M., & Wolfson, D. (1985); The Halstead-Reitan Neuropsychological Test Battery: Theory and clinical interpretation. Tucson: Neuropsychology).

The Tapping Speed test has been included for two reasons. First, there is a need to incorporate a measure of performance that can serve as a covariate by which "motor" effect can be partialed out from "cognitive" effects. Second, the inclusion of Tapping Speed fulfils the recommendation made in the CPMP EWP's guidance that "timed performance tasks" be included as secondary outcome measures. Drug effects on tapping speed would in and of themselves provide useful evidence of drug efficacy. Such a task perhaps also has the propensity to serve as a laboratory model of bradykinesia.

Tests 5—Simple Reaction Time (SRT)

The Reaction Time test is a classic test used to assess psychomotor speed. The appearance of the stimulus is completely visual (unlike Set Shifting Test where an auditory tone is also heard) and occurs after a random delay from the presentation of a crosshair (centred both horizontally and vertically on the screen) that is used to centre the participants' eyes prior to the onset of the stimulus. There are two different phases to this test, namely the practice phase and the main trials phase. The practice phase enables the participant to become familiar with the test and to reach a stable baseline before advancing to the main trials. 24 stimuli are presented, and the participant needs to achieve a criterion of at least 20 correct in order to advance. Feedback is provided throughout the course of this phase. The participant has three such attempts to pass this phase otherwise the test advances to the end screen and then the test quits. If the practice criterion is achieved then the main trials are presented. Two sets of 50 trials are presented in the same manner, which allows the participant a brief rest midway through the test session. Response is by pressing spacebar. The summary Variables are: How many times the practice session is done; Number of early responses; Number of trials in which no response occurred; Number of the trials completed; Number of trials completed for the right; Total number of correct answers; Mean of correct reaction times; Mean of incorrect reaction times; Standard deviation of the correct reaction times.

Test 6—Choice Reaction Time (CRT)

The Reaction Time test is a classic test used to assess psychomotor speed and this test in particular measures choice reaction time. In this test participants are instructed to respond by pressing keys on the left or the right hand side of the keyboard corresponding to the side of the screen on which a red or green circle (the stimulus) appears. The appearance of the stimulus is completely visual (unlike Set Shifting Test where an auditory tone is also heard) and occurs after a random delay from the presentation of a crosshair (centred both horizontally and vertically on the screen) that is used to centre the participants' eyes prior to the onset of the stimulus. There are two different phases to this test, namely the practice phase and the main trials phase. The practice phase enables the participant to become familiar with the test and to reach a stable baseline before advancing to the main trials. 20 stimuli are presented randomly to the left or the right of the screen and the participant needs to achieve a criterion of at least 16 out of 20 in order to advance. Feedback is provided throughout the course of this phase. The participant has three such attempts to pass this phase otherwise the test advances to the end screen and then the test quits. If the practice criterion is achieved then the main trials are presented. 100 trials are presented in the same manner i.e. stimuli appear randomly to the left or the right of the crosshairs after a random pause varying between 750 ms and 1500 ms. There are no cut-off criteria and no feedback offered during this phase of the test. The subject should place his right index finger on the red key, which will replace the "/" key of a British keyboard. He/she should place his left index finger on the green key, which will replace the "z" key of a British keyboard. Response is by pressing either key corresponding to which side of the screen the circle appears. The examiner moves the test by pressing the left button of the mouse.

Example 2

Clinical Protocol

A double blind Phase III study, placebo controlled, parallel-group, randomized, multinational was conducted comparing 2 oral doses of Safinamide versus placebo. The placebo group was constituted by patients treated with a stable dose of a dopamine agonist. The dopamine agonist could have been any of the ones used in clinical practice, according to clinical procedures in the different countries. 269 patients (~90 per arm), were enrolled and treated for six months. Primary efficacy variable was UPDRS III. All the randomized patients were tested for cognitive impairment with Cogtest at Screening, Baseline, week 12 and week 24 (or early discontinuation).

Results

Baseline data revealed significant impairment across cognitive domains for the entire sample, compared to Cogtest Healthy Volunteer Sample. Executive function and the non verbal working memory showing most impairment.

The control group, treated with the DA alone, showed deterioration over time in line with what expected by this kind of treatment. Both groups, treated with low and high dose of safinamide, showed significant improvement from baseline for several cognitive variables at three and six months evaluation times. This effect was most marked for executive function (reasoning and problem solving).

As explicative example of the effect of safinamide, data in the "Strategic Target Detection" test showed a significant improvement in the observed score (Z-score) in both treated groups (low and high dose of safinamide) from baseline to both three and six months.

The invention claimed is:

1. A method of improving cognitive function and treating cognitive impairment, the method consisting essentially of administering to a patient in need thereof a therapeutically effective amount of a compound consisting of an alpha-aminoamide of formula (I),

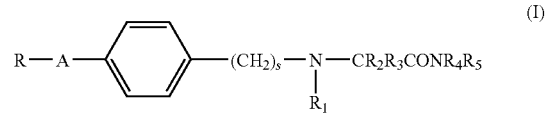

wherein:
A is a —$(CH_2)_n$—X-group, wherein n is an integer of 0 to 5, and X is $CH_2$, —O—, —S— or —NH—;
s is 1 or 2;
R is a furyl, thienyl, pyridyl ring or a phenyl ring, optionally substituted by one or two substituents independently selected from halogen, hydroxy, cyano, $C_1$-$C_6$ alkyl, $C_1$-$C_6$ alkoxy or trifluoromethyl;
$R_1$ is hydrogen or $C_1$-$C_6$ alkyl or $C_3$-$C_7$ cycloalkyl;
one of $R_2$ and $R_3$ is hydrogen, and the other is $C_1$-$C_4$ alkyl, optionally substituted by hydroxy or phenyl; phenyl, optionally substituted by one or two substituents independently selected from $C_1$-$C_6$ alkyl, halogen, hydroxy, $C_1$-$C_6$ alkoxy or trifluoromethyl; or $R_2$ and $R_3$, taken with the carbon atom which they are linked to, form a $C_3$-$C_6$ cycloalkyl ring;
$R_4$ and $R_5$ are independently hydrogen, $C_1$-$C_6$ alkyl or $C_3$-$C_7$ cycloalkyl; or $R_4$ and $R_5$, taken together with the nitrogen atom they are linked to, form a 5 to 7 atom saturated heterocyclic ring; and
isomers, mixtures, and pharmaceutically acceptable salts or esters thereof.

2. The method according to claim 1, wherein A is selected from —$CH_2$—, —$CH_2$—$CH_2$—, —$CH_2$—S—, —$CH_2$—$CH_2$—S— or —$(CH_2)_n$—O—;
n is an integer from 0 to 5;
s is 1 or 2;
R is a phenyl ring, optionally substituted by one or two substituents independently selected from halogen, trifluoromethyl, methoxy or thienyl ring;
$R_1$ is hydrogen or $C_1$-$C_4$ alkyl;
one of $R_2$ and $R_3$ is hydrogen and the other is $C_1$-$C_4$ alkyl, optionally substituted by hydroxyl, phenyl, or phenyl, optionally substituted by one or two halogen atoms, or $R_2$ and $R_3$ together can form with the atom they are linked to a cyclopropyl or a cyclopentyl ring;
$R_4$ and $R_5$ are hydrogen or $C_1$-$C_4$ alkyl or together with the nitrogen they are linked to form a pyrrolidine or piperidine ring.

3. The method according to claim 1, wherein said compound is administered at a dose ranging from about 0.3 to about 100 mg/kg body weight per day.

4. The method according to claim 1, wherein said compound is selected from the group consisting of:
2-(4-Benzyloxybenzylamino)-propanamide;
2-[4-(2-Methoxybenzyloxy)-benzylamino]-propanamide;
2-[4-(2-Fluorobenzyloxy)-benzylamino]-propanamide;
(S)-(+)-2-[4-(2-Fluorobenzyloxy)-benzylamino]-propanamide;

(R)-(−)-2-[4-(2-Fluorobenzyloxy)-benzylamino]-propanamide;
2-[4-(2-Fluorobenzyloxy)-benzylamino]-N-methyl-propanamide;
N-{2-[4-(2-Fluorobenzyloxy)-benzylamino]}-propionyl-pyrrolidine;
2-[4-(3-Methoxybenzyloxy)-benzylamino]-propanamide;
2-[4-(3-Cyanobenzyloxy)-benzylamino]-propanamide;
2-[4-(3-Fluorobenzyloxy)-benzylamino]-propanamide;
(S)-(+)-2-[4-(3-Fluorobenzyloxy)-benzylamino]-propanamide;
(R)-(−)-2-[4-(3-Fluorobenzyloxy)-benzylamino]-propanamide;
2-[4-(3-Fluorobenzyloxy)-benzylamino]-N-methyl-propanamide;
N-{2-[4-(3-Fluorobenzyloxy)-benzylamino]}-propionyl-pyrrolidine;
2-[4-(4-Fluorobenzyloxy)-benzylamino]-propanamide;
2-[4-(2-Chlorobenzyloxy)-benzylamino]-propanamide;
(S)-(+)-2-[4-(2-Chlorobenzyloxy)-benzylamino]-propanamide;
(R)-(−)-2-[4-(2-Chlorobenzyloxy)-benzylamino]-propanamide;
2-[4-(3-Chlorobenzyloxy)-benzylamino]-propanamide;
(S)-(+)-2-[4-(3-Chlorobenzyloxy)-benzylamino]-propanamide;
(R)-(−)-2-[4-(3-Chlorobenzyloxy)-benzylamino]-propanamide;
2-(4-Benzyloxybenzylamino)-3-hydroxy-propanamide;
2-[4-(2-Fluorobenzyloxy)-benzylamino]-3-hydroxy-propanamide;
2-[4-(3-Fluorobenzyloxy)-benzylamino]-3-hydroxy-propanamide;
2-(4-Benzyloxybenzylamino)-3-hydroxy-N-methyl-propanamide;
2-[4-(2-Fluorobenzyloxy)-benzylamino]-3-hydroxy-N-methyl-propanamide;
2-[4-(3-Fluorobenzyloxy)-benzylamino]-3-hydroxy-N-methyl-propanamide;
2-[4-(2-Chlorobenzyloxy)-benzylamino]-3-hydroxy-N-methyl-propanamide;
2-[4-(3-Cyanobenzyloxy)-benzylamino]-3-hydroxy-N-methyl-propanamide;
2-[4-(2-Fluorobenzyloxy)-phenylethylamino]-propanamide;
2-[4-(3-Fluorobenzyloxy)-phenylethylamino]-propanamide;
2-[4-(2-Chlorobenzyloxy)-phenylethylamino]-propanamide;
2-[4-(3-Chlorobenzyloxy)-phenylethylamino]-propanamide;
2-{4-[2-(3-Fluorophenyl)-ethyloxy]benzylamino}-propanamide;
2-{4-[2-(3-Fluorophenyl)-ethyl]benzylamino}-propanamide;
2-[N-(4-Benzyloxybenzyl)-N-methylamino]-propanamide;
2-{4-[(3-Chlorobenzyloxy)-phenylethyl]-amino}-propanamide;
2-[4-Benzylthiobenzylamino]-propanamide;
2-[4-(2-Fluorobenzylthio)-benzylamino]-propanamide;
2-[4-(2-Chlorobenzylthio)-benzylamino]-propanamide;
2-[4-(3-Fluorobenzylthio)-benzylamino]-propanamide;
2-[4-(3-Chlorobenzylthio)-benzylamino]-propanamide;
2-[4-(3-Phenylpropoxy)-benzylamino]-propanamide;
2-[4-(4-Phenylbutoxy)-benzylamino]-propanamide;
2-[4-(5-Phenylpentoxy)-benzylamino]-propanamide;
2-(4-Benzyloxybenzylamino)-3-phenyl-N-methyl-propanamide;
2-(4-Benzyloxybenzylamino)-3-methyl-N-methyl-butanamide;
2-(4-Benzyloxybenzylamino)-2-phenyl-acetamide;
2-[4-(2-Fluorobenzyloxy)-benzylamino]-2-phenyl-acetamide;
2-[4-(3-Fluorobenzyloxy)-benzylamino]-2-phenyl-acetamide;
2-[4-(2-Fluorobenzyloxy)-benzyl-N-methylamino]-2-phenyl-acetamide;
2-[4-(3-Fluorobenzyloxy)-benzyl-N-methylamino]-2-phenyl-acetamide;
2-[4-(3-Chlorobenzyloxy)-benzylamino]-2-phenyl-acetamide;
2-[4-(2-Fluorobenzyloxy)-benzylamino]-2-(2-fluorophenyl)-acetamide;
2-[4-(2-Fluorobenzyloxy)-benzylamino]-2-(3-fluorophenyl)-acetamide;
2-[4-(3-Fluorobenzyloxy)-benzylamino]-2-(2-fluorophenyl)-acetamide;
2-[4-(3-Fluorobenzyloxy)-benzylamino]-2-(3-fluorophenyl)-acetamide;
2-[4-(3-Chlorobenzyloxy)-benzylamino]-2-(3-fluorophenyl)-acetamide;
2-(4-(2-Thienyloxy)-benzylamino)-propanamide;
and isomers, mixtures, and pharmaceutically acceptable salts thereof.

5. The method according to claim 1, wherein the compound is (S)-(+)-2-[4-(2-Fluorobenzyloxy)-benzylamino]-propanamide.

6. The method according to claim 1, wherein the compound is (S)-(+)-2-[4-(3-Fluorobenzyloxy)-benzylamino]-propanamide.

7. The method according to claim 1, wherein the cognitive impairment is associated with a disease selected from the group consisting of autism, dyslexia, attention deficit hyperactivity disorder, anxiety, schizophrenia, obsessive compulsive disorders, psychosis, bipolar disorders, depression, Tourette's syndrome, Mild Cognitive Impairment (MCI) and disorders of learning in children, adolescents and adults, Age Associated Memory Impairment, Age Associated Cognitive Decline, Alzheimer's Disease, Down's Syndrome, traumatic brain injury Huntington's Disease, Progressive Supranuclear Palsy (PSP), HIV, stroke, vascular diseases, Pick's or Creutzfeldt-Jacob disease, multiple sclerosis (MS) white matter disorders and drug-induced cognitive worsening.

8. The method according to claim 1, wherein the cognitive impairment is associated with a disease selected from the group consisting of autism, dyslexia, attention deficit hyperactivity disorder, anxiety, schizophrenia, obsessive compulsive disorders, psychosis, bipolar disorders, Tourette's syndrome, Mild Cognitive Impairment (MCI) and disorders of learning in children, adolescents and adults, Age associated Memory Impairment, Age associated Cognitive Decline, Down's Syndrome, HIV and vascular diseases.

9. A method of improving cognitive function and treating cognitive impairment, wherein the cognitive impairment is associated with a disease selected from the group consisting of autism, dyslexia, attention deficit hyperactivity disorder, anxiety, schizophrenia, obsessive compulsive disorders, psychosis, bipolar disorders, depression, Tourette's syndrome, Mild Cognitive Impairment (MCI) and disorders of learning in children, adolescents and adults, Age Associated Memory Impairment, Age Associated Cognitive Decline, Alzheimer's Disease, Down's Syndrome, traumatic brain injury Huntington's Disease, Progressive Supranuclear Palsy (PSP), HIV, stroke, vascular diseases, Pick's or Creutzfeldt-Jacob disease, multiple sclerosis (MS) white matter disorders and drug-induced cognitive worsening, the method consisting essentially of administering to a patient in need thereof a combination therapy consisting of cholinesterase inhibitors and/or acetylcholine modulators with a therapeutically effective amount of an alpha-aminoamide compound of formula (I),

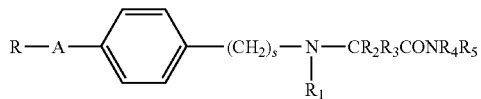
(I)

wherein:

A is a —$(CH_2)_n$—X-group, wherein n is an integer of 0 to 5, and X is $CH_2$, —O—, —S— or —NH—;

s is 1 or 2;

R is a furyl, thienyl, pyridyl ring or a phenyl ring, optionally substituted by one or two substituents independently selected from halogen, hydroxy, cyano, $C_1$-$C_6$ alkyl, $C_1$-$C_6$ alkoxy or trifluoromethyl;

$R_1$ is hydrogen or $C_1$-$C_6$ alkyl or $C_3$-$C_7$ cycloalkyl;

one of $R_2$ and $R_3$ is hydrogen, and the other is $C_1$-$C_4$ alkyl, optionally substituted by hydroxy or phenyl; phenyl, optionally substituted by one or two substituents independently selected from $C_1$-$C_6$ alkyl, halogen, hydroxy, $C_1$-$C_6$ alkoxy or trifluoromethyl; or $R_2$ and $R_3$, taken with the carbon atom which they are linked to, form a $C_3$-$C_6$ cycloalkyl ring;

$R_4$ and $R_5$ are independently hydrogen, $C_1$-$C_6$ alkyl or $C_3$-$C_7$ cycloalkyl; or $R_4$ and $R_5$, taken together with the nitrogen atom they are linked to, form a 5 to 7 atom saturated heterocyclic ring; and isomers, mixtures, and pharmaceutically acceptable salts or esters thereof.

10. The method according to claim 9, wherein the compound is (S)-(+)-2-[4-(2-Fluorobenzyloxy)-benzylamino]-propanamide.

11. The method according to claim 9, wherein the compound is (S)-(+)-2-[4-(3-Fluorobenzyloxy)-benzylamino]-propanamide.

* * * * *